United States Patent
Poulard

(10) Patent No.: US 8,430,271 B2
(45) Date of Patent: Apr. 30, 2013

(54) FLUID PRODUCT DISPENSER

(75) Inventor: Fabien Poulard, Rouen (FR)

(73) Assignee: Aptar France SAS, Le Neubourg (FR)

( * ) Notice: Subject to any disclaimer, the term of this patent is extended or adjusted under 35 U.S.C. 154(b) by 78 days.

(21) Appl. No.: 13/212,979

(22) Filed: Aug. 18, 2011

(65) Prior Publication Data

US 2011/0303700 A1 Dec. 15, 2011

Related U.S. Application Data

(62) Division of application No. 11/629,219, filed as application No. PCT/FR2005/050438 on Jun. 13, 2005, now abandoned.

(30) Foreign Application Priority Data

Jun. 14, 2004 (FR) ...................... 04 51164

(51) Int. Cl.
*B67D 7/84* (2010.01)
*B67D 7/22* (2010.01)
*A61M 11/00* (2006.01)

(52) U.S. Cl.
USPC ......... 222/162; 222/160; 222/36; 128/200.23

(58) Field of Classification Search .................. 222/235, 222/254, 162, 160, 183, 36, 38, 164, 167, 222/168; 128/200.14, 200.17, 200.23
See application file for complete search history.

(56) References Cited

U.S. PATENT DOCUMENTS

| | | | |
|---|---|---|---|
| 1,032,861 A * | 7/1912 | Powell ........................ 222/130 |
| 2,319,739 A | 5/1943 | Kessler | |
| 2,998,165 A | 8/1961 | De Elorza | |
| 3,191,867 A * | 6/1965 | Lee ............................. 239/288.5 |
| 3,334,627 A * | 8/1967 | Gorman ................... 128/200.23 |
| 3,490,177 A | 1/1970 | Perrion | |
| 3,994,421 A * | 11/1976 | Hansen ......................... 222/182 |
| 4,637,528 A * | 1/1987 | Wachinski et al. ........... 222/182 |
| 4,938,240 A | 7/1990 | Lakhan et al. | |
| 5,020,527 A * | 6/1991 | Dessertine ............... 128/200.23 |
| 5,297,697 A | 3/1994 | Boring | |
| 6,681,950 B2 | 1/2004 | Miller et al. | |
| 7,886,934 B2 | 2/2011 | Lu et al. | |
| 2003/0141325 A1 | 7/2003 | Balogh | |
| 2006/0175345 A1 | 8/2006 | Lu et al. | |
| 2008/0087279 A1* | 4/2008 | Tieck et al. ............... 128/200.23 |

FOREIGN PATENT DOCUMENTS

| | | |
|---|---|---|
| EP | 0 839 544 A2 | 5/1998 |
| EP | 1 163 922 A2 | 12/2001 |
| FR | 1 113 454 A | 3/1956 |
| GB | 11635 A | 0/1911 |

* cited by examiner

*Primary Examiner* — Paul R Durand
*Assistant Examiner* — Benjamin R Shaw
(74) *Attorney, Agent, or Firm* — Sughrue Mion, PLLC

(57) ABSTRACT

A fluid dispenser device comprising: a reservoir (1) of fluid to be dispensed; a dispenser member (2), such as a pump or a valve, mounted on said reservoir (1); and a body (3) that is suitable for receiving said reservoir (1), said body (3) being provided with a dispenser orifice and with an opening (310) via which said reservoir (1) can be inserted into the body (3), said reservoir (1) being displaceable between a working position, in which said dispenser member (2) co-operates with said body (3) between a rest position and a dispensing position, and a withdrawn position in which said dispenser member (2) does not co-operate with said body (3), said reservoir (1) being secured to said body (3) in all positions.

13 Claims, 2 Drawing Sheets

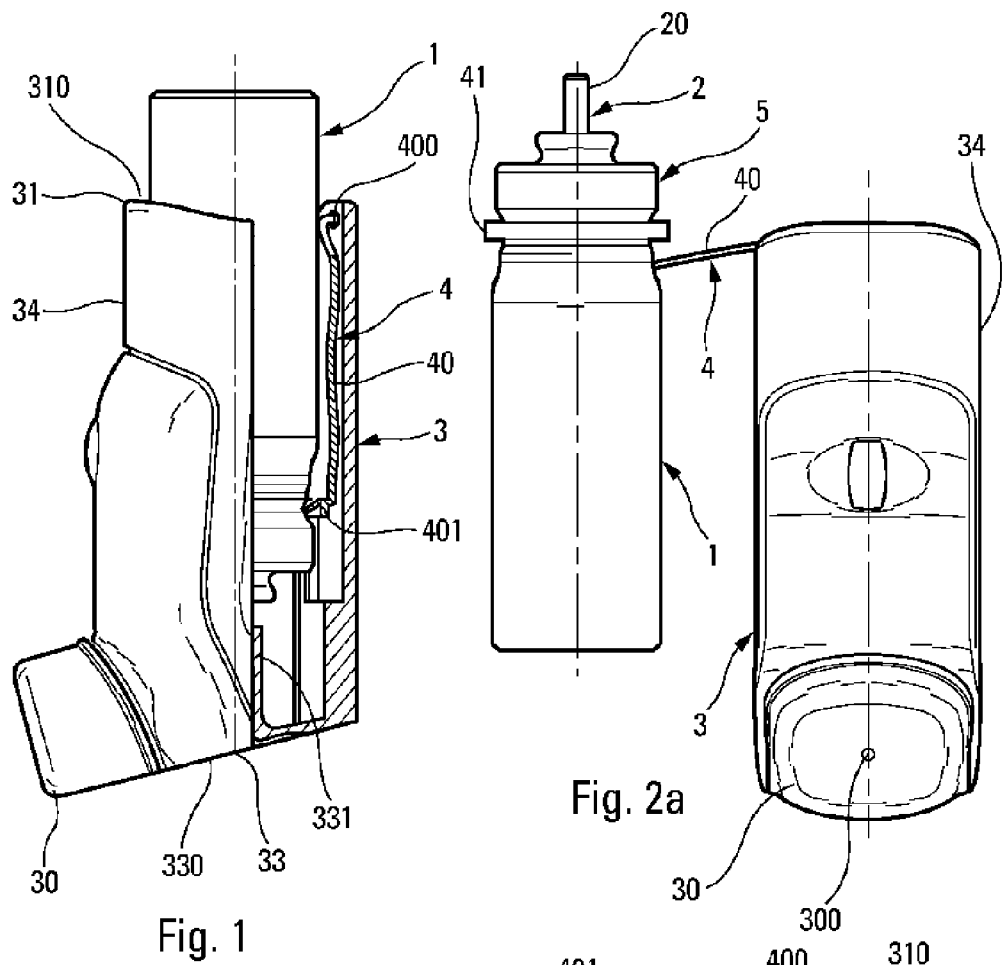
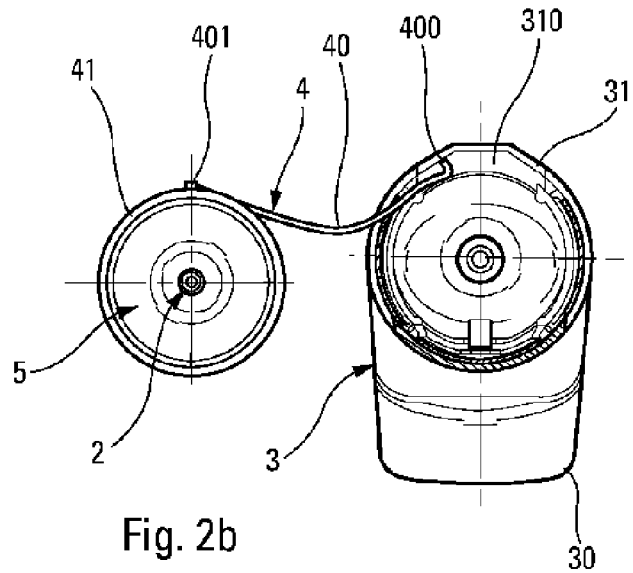

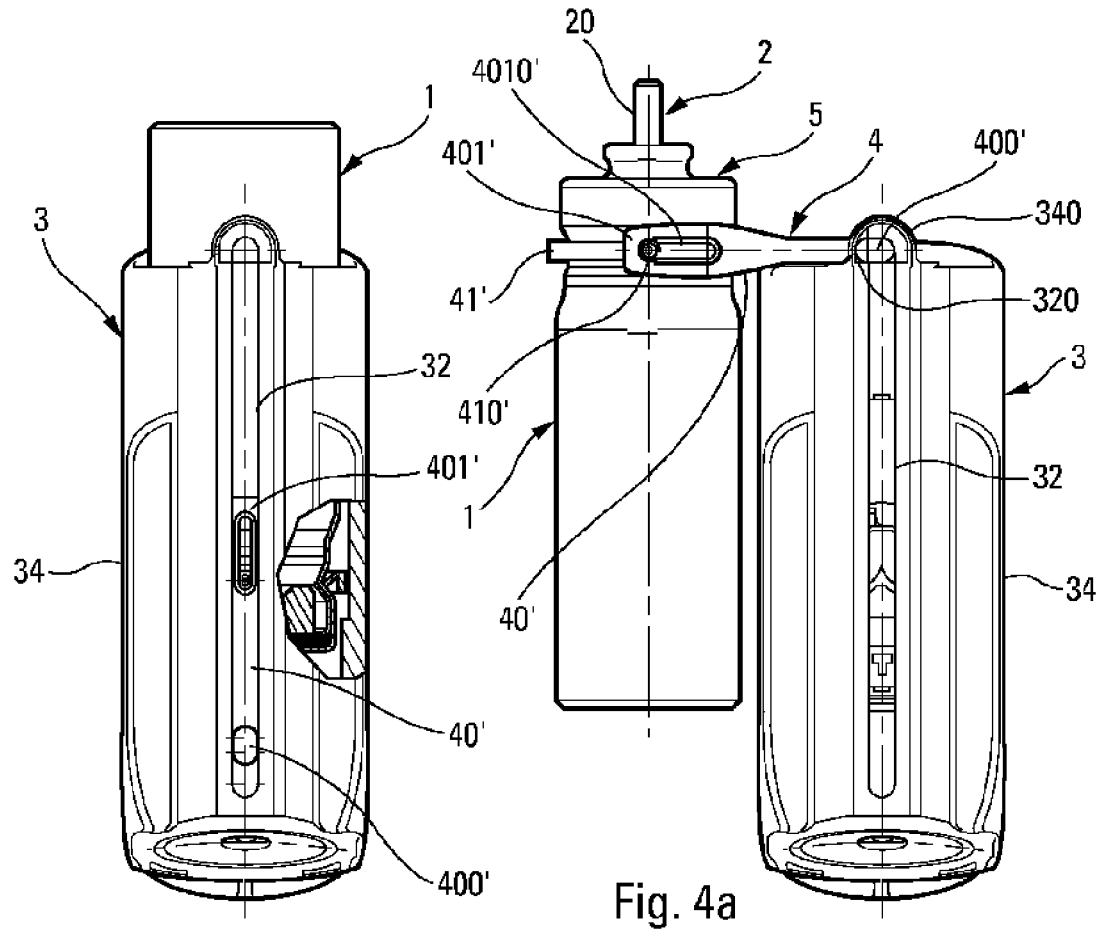
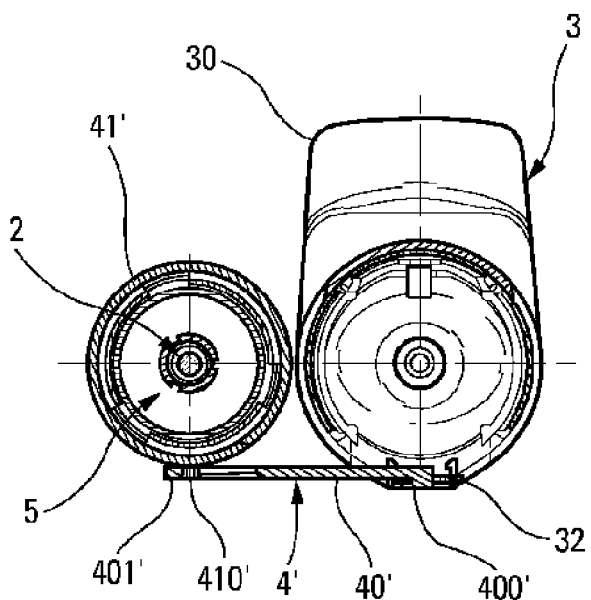

FLUID PRODUCT DISPENSER

CROSS REFERENCE TO RELATED APPLICATIONS

This is a divisional of U.S. application Ser. No. 11/629,216 filed Dec. 12, 2006 which was a §371 National Stage Application of PCT/FR2005/050438 filed Jun. 13, 2005 and which claims priority from French Application No. 04/51164 filed Jun. 14, 2004. The entire disclosure of the prior applications are hereby incorporated by reference.

The present invention relates to a fluid dispenser device.

Advantageous fields of application of such a device are particularly, but not exclusively, the fields of pharmacy, cosmetics, and perfumery.

Dispenser devices of the prior art generally comprise a fluid reservoir on which there is mounted a dispenser member such as a pump or a valve. The dispenser member generally comprises a metering chamber in which an actuator rod or a valve member is slidably mounted. In particular for aerosol devices in which the fluid is expelled by means of a propellant gas through a metering valve, the reservoir is generally slidably mounted in the body so as to actuate the valve member. Connecting the body to the valve member mounted on the reservoir defines a working position of the device in which said valve member co-operates with the body. In the working position, the valve member is thus displaceable between a rest position and a dispensing position following actuation by the user. Generally, it is necessary, after several actuations of the valve member, to clean the interface between the valve member and the body. Residue of dispensed fluid may be deposited on the walls of the connection sleeve co-operating with the valve member. Unfortunately, the residue is capable of polluting the fluid that remains to be dispensed from the reservoir, indeed it is even capable of hindering the expulsion of the fluid. For such cleaning, the user must thus disengage the valve member from the connection sleeve and remove the reservoir from the body. Such disengagement thus results in a withdrawn position of the device in which the valve member does not co-operate with the body. The body and the reservoir are thus likely to be mislaid, or, following a cleaning operation, there is even a risk of swapping over bodies and reservoirs belonging to different users. Such a situation can occur in particular in hospital care services in which large numbers of dispenser devices are cleaned. Thus, if two reservoirs are swapped over, there exist possible risks of problems of hygiene and in particular microbiological contamination for the user, in particular when the dispenser device is a dispenser device using a mouthpiece. In addition, if reservoirs that do not carry information regarding the identity of the fluid that they contain are mixed up, then the user of a pharmaceutical might absorb or inhale a wrong fluid, e.g. having allergic effects or effects that are likely to generate incompatibilities between medicines. Swapping over two reservoirs after cleaning is particularly dangerous when the device is provided with a dose counter or indicator. A reservoir mix up could have dramatic consequences if the user ends up with a counter displaying a number of doses for dispensing that is greater than the number of doses actually remaining in the reservoir. The user thus risks ending up with an empty reservoir, while the counter indicates that doses remain to be dispensed. The risk to health is thus very significant.

An object of the present invention is to provide a dispenser device that does not have the above-mentioned drawbacks.

More particularly, an object of the present invention is to provide a dispenser device that is simple and inexpensive to manufacture and to assemble.

The present invention thus provides a fluid dispenser device comprising: a reservoir of fluid to be dispensed; a dispenser member, such as a pump or a valve, mounted on said reservoir; and a body that is suitable for receiving said reservoir, said body being provided with a dispenser orifice and with an opening via which said reservoir can be inserted into the body, said reservoir being displaceable between a working position, in which said dispenser member co-operates with said body between a rest position and a dispensing position, and a withdrawn position in which said dispenser member does not co-operate with said body, said reservoir being secured to said body in all positions. Thus, the reservoir and the dispenser member are connected to the body in permanent manner, such that it is impossible to swap over reservoirs accidentally after cleaning, when they are put back into place in the body.

Advantageously, said reservoir is connected to said body by deformable and/or displaceable connection means, enabling said reservoir to be inseparable from said body.

In a first variant embodiment, said connection means comprise a flexible cord connecting said body and said reservoir.

Advantageously, said flexible cord is fastened to the body in the proximity of said opening.

In a second variant embodiment, said connection means comprise a rod, in particular a rigid rod, connecting said body and said reservoir, said rod including a first end that is slidably mounted in a guide rail formed over at least a fraction of the height of said body, and a second end connected to said reservoir.

Advantageously, said rod is displaceable in translation and in rotation relative to said body.

Advantageously, said reservoir is movable relative to said rod.

Advantageously, said connection means include a fastener ring that is suitable for being fastened, engaged, and/or snap-fastened on said reservoir.

Advantageously, said connection means enable the body and the reservoir to be positioned side by side, when said reservoir is in its withdrawn position, thereby releasing the entire surface of the opening of the body.

Advantageously, said body is provided with a counter or indicator device for counting or indicating the number of doses of fluid that have been dispensed or that remain to be dispensed from the reservoir.

In an advantageous characteristic of the invention, said indicator or counter device is actuated by the reservoir being displaced between its rest and dispensing positions.

Other characteristics and advantages of the present invention appear more clearly from the following detailed description of two embodiments of the invention, given by way of non-limiting example, and with reference to the accompanying drawings, and in which:

FIG. 1 is a partially cut-away diagrammatic side view of a dispenser device constituting a first embodiment of the invention, with a reservoir in its working position;

FIG. 2a is a diagrammatic front view of the FIG. 1 dispenser device, with a reservoir in its withdrawn position;

FIG. 2b is a diagrammatic plan view of the FIG. 2a dispenser device;

FIG. 3 is a partially cut-away diagrammatic rear view of a dispenser device constituting a second embodiment of the invention, with a reservoir in its working position;

FIG. 4a is a diagrammatic rear view of the FIG. 3 dispenser device, with a reservoir in its withdrawn position; and FIG. 4b is a diagrammatic plan view of the dispenser device shown in FIG. 4a.

In the present invention, the dispenser device advantageously comprises five component elements, namely a reservoir 1, a dispenser member 2, a fastener member 5, a body 3, and connection means 4.

The reservoir 1 can present any appropriate shape. The reservoir includes a generally-cylindrical cylinder that is provided with a bottom end closed by a bottom wall, and with a top end from which there projects a neck. The neck defines an open passage for putting the inside of the reservoir into communication with the outside atmosphere. The reservoir can contain fluid at atmospheric pressure or fluid that is under pressure.

The dispenser member 2 can be a pump or a valve, preferably a metering valve, of which the function is not explained in greater detail below. For a valve, generally used with devices of the aerosol type, a valve member 20 is provided that is displaceable in a metering chamber so as to expel the dose of fluid by means of a propellant gas. The reservoir 1 is mounted to slide axially in said body. This axial displacement drives displacement of the valve member, and therefore actuates the valve, thereby enabling said metering chamber to be emptied.

The fastener member 5 has the function of fastening the dispenser member 2 on the reservoir 3. The member 5 can be fastened on the neck of the reservoir in known manner by crimping, snap-fastening, screw-fastening, or the like.

In the embodiment shown in the various figures, the body 3 is a typical body for an inhaler. The body comprises a substantially-cylindrical shell 34 including a top end 31 defining an opening 310, and a bottom end 33 closed by a substantially oblique wall 330. An endpiece 30 provided with a dispenser orifice 300 is disposed in the extension of the oblique wall 330 and projects outwards from the shell 34. A connection sleeve 331 projects upwards from the bottom end 33 of the body. It should be observed that the body as described is merely one embodiment. Bodies of any other configuration could very well be envisaged, such as configurations that are conventionally used for nasal or otological applications, or even in the field of perfumery or cosmetics.

The reservoir 1 is inserted into the body 3 via the opening 310. Then, the reservoir 1 is mounted in its working position on the body 3 by engaging the actuator rod 20 in the connection sleeve 331. In the present embodiment, the dispenser device shown can be actuated in conventional manner by pressing on the bottom wall of the reservoir. In the "working" position of the reservoir, the valve 2 co-operates with the body 3 between a rest position and a dispensing position. The rest position corresponds to the position of the valve member 20 in the sleeve 331 when the valve 2 is not driven by the device being actuated by the user. The dispensing position corresponds to the position of the valve member 20 in the sleeve 331 when the device is being actuated by the user. The reservoir 1 also defines a withdrawn position when the valve member 20 is disengaged from the connection sleeve 331 and the reservoir is removed from the body 3. In this event, the dispenser member 2 no longer co-operates with the body 3 and therefore can no longer be actuated by the user.

In the invention, connection means 4, 4' are provided so as to secure the reservoir 1 to the body 3 in all positions. In this embodiment, the term "reservoir" encompasses the reservoir, the dispenser member, and the fastener member which are assembled together, as described above. Thus, the reservoir 1, the dispenser member 2, and the fastener member 5 could be connected in permanent manner to the body 3, even in the withdrawn position of said dispenser member 2.

By way of example, two variant embodiments of the connection means 4, 4' can be envisaged.

In a first variant embodiment shown in FIGS. 1, 2a, and 2b, the connection means 4 comprise a flexible cord 40. The cord presents a certain degree of deformability or of elasticity so as to be able to fold and/or stretch easily. The cord includes a first end 400 and a second end 401. The two ends 400, 401 are respectively connected to the body 3 and to the reservoir 1. The ends 400, 401 can be made integrally with the body and/or the reservoir, or they can be add-on parts that are fastened by any appropriate means to a corresponding surface or in a corresponding housing. The end 400 is advantageously fastened to the shell 34 in the proximity of the opening 310. The end 401 itself is advantageously connected to a fastener ring 41 that is suitable for being fastened, engaged, and/or snap-fastened on the reservoir 1, as can be seen in particular in FIG. 2b. In this embodiment, the ring 41 can be housed below the fastener member 5, and it is thus confined in a space located between the reservoir 1 and the fastener member 5.

In order to pass from a working position shown in FIG. 1 to a withdrawn position shown in FIGS. 2a and 2b, the user exerts traction on the reservoir so as to disengage the rod 20 from the sleeve 331. The flexibility of the cord 40 thus enables the reservoir 1 to be removed from the body 3, and thus releases access to the inside of the body 3 by completely clearing the surface of the opening 310 of the body. The reservoir 1 and the body 3, that are movable relative to each other, can thus be positioned side by side, so as not to hinder access to the sleeve 331 to be cleaned.

In a second variant embodiment shown in FIGS. 3, 4a, and 4b, the connection means 4' comprise a rod or connection bar 40', preferably a rigid rod or connection bar, including a first end 400' and a second end 401'. The two ends 400', 401' are respectively connected to the body 3 and to the reservoir 1. The first end 400' is slidably mounted in a kind of guide rail 32 formed over at least a fraction of the height of the body 3, so as to enable the reservoir to be displaced vertically relative to the body. In a particular embodiment, the second end 401' itself includes a longitudinal slot 4010' in which there is slidably mounted a connection element 410' connected to a fastener ring 41' fastened to the reservoir. As in the above-described variant embodiment, the fastener ring 41' can be housed in a space situated between the fastener member 5 and the reservoir 1. In similar manner, the ring can be fastened, engaged, snap-fastened, or the like on said reservoir. It should be observed that the connection element 410' can be assembled on the fastener ring 41' in such a manner as to be removable, e.g. by unscrewing.

In order to pass from a working position shown in FIG. 3 to a withdrawn position shown in FIGS. 4a and 4b, the user must exert traction on the reservoir 1 so as to displace the reservoir 1 relative to the body 3 by sliding the first end 400' of the rod or connection bar 40' in the guide rail 32. At the end of sliding, the first end 400' reaches a turn ring 340 that is suitable for causing the rod 40' to turn, e.g. through 90°. Such turning can be limited by an adjacent transverse edge 320 of the rail 32. By way of example, the transverse edge can correspond to a portion of the top end of the body 3, as can be seen in particular in FIG. 4a. Such turning thus clears access to the inside of the body 3, and thus releases the surface of the opening 310 of the body 3. Then, the connection element 410' can be displaced along the slot 4010' so as to offset the reservoir 1 relative to the body 3 and thus enable the reservoir 1 to turn, e.g. through approximately 180°, so as to become positioned side by side with the body 3. Thus, neither the connection means 4 nor the reservoir 1 hinders access to the body 3, and in particular to the connection sleeve 331 to be cleaned.

In a particularly advantageous embodiment, the body 3 can be provided with a counter or indicator device for counting or indicating the number of doses of fluid that have been dispensed or that remain to be dispensed from the reservoir 1. For example, the counter or indicator device can be actuated by the reservoir being displaced between its rest and dispensing positions. By means of the presence of connection means 4, 4', the user or the person responsible for cleaning the device cannot accidentally swap over reservoirs after cleaning. Consequently, the reservoir is always necessarily associated with its own body, and the number of doses indicated on the body necessarily corresponds to the correct number of doses that have been dispensed or that remain to be dispensed from the reservoir.

Although the present invention is described above with reference to a particular embodiment thereof, it is clear that it is not limited by said embodiment. On the contrary, any useful modification can be applied thereto by the person skilled in the art, without going beyond the ambit of the present invention, as defined by the accompanying claims.

What is claimed is:

1. A fluid dispenser device comprising:
    a reservoir (1) of fluid to be dispensed;
    a dispenser member (2) mounted on said reservoir (1);
    a body (3) for receiving said reservoir (1), said body (3) having a bottom end (33) provided with a dispenser orifice and a top end provided with an opening (310), said reservoir (1) being inserted into the body (3) through said opening, said reservoir (1) being displaceable between working positions, in which said dispenser member (2) co-operates with said body (3) between a rest position and a dispensing position, said reservoir being axially slidable in said body (3) between said rest and dispensing positions, and a withdrawn position in which said dispenser member (2) is not inserted into said body (3);
    connection means for securing said reservoir to said body in each of the rest position, the dispensing position, and the withdrawn position; and
    said connection means comprising a rigid rod (40') connecting said body (3) to said reservoir (1), said rod (40') including a first end (400') that is slidably mounted in a guide rail (32) formed over at least a fraction of the height of said body (3), and a second end (401') connected to said reservoir (1).

2. A dispenser device according to claim 1, in which said rigid rod (40') is displaceable in translation and in rotation relative to said body (3).

3. A dispenser device according to claim 1, in which said reservoir (1) is movable relative to said rigid rod (40').

4. A dispenser device according to claim 1, wherein the second end (401') of the rigid rod is attached to the reservoir by a fastener ring (41').

5. A dispenser device according to claim 1, in which said connection means (4, 4') enable the body (3) and the reservoir (1) to be positioned side by side, when said reservoir (1) is in its withdrawn position, thereby freeing an entire surface of the opening of the body (3).

6. A dispenser device according to claim 1, in which said body (3) is provided with a counter or indicator device for counting or indicating the number of doses of fluid that have been dispensed or that remain to be dispensed from the reservoir.

7. A dispenser device according to claim 6, in which said indicator or counter device is actuated by the reservoir being displaced between its rest and dispensing positions.

8. The dispenser device according to claim 1, wherein the dispenser member is a pump or a valve.

9. A fluid dispenser device comprising:
    a reservoir of fluid to be dispensed;
    a dispenser member mounted on said reservoir;
    a body configured to receive the reservoir, the body comprising a bottom end comprising a dispenser orifice and a top end comprising an opening through which the reservoir is inserted to be received in the body, the reservoir displaceable between working positions, in which the dispenser member co-operates with the body between a rest position and a dispensing position, the reservoir axially slidable in the body between the rest position and the dispensing position, and a withdrawn position in which the dispenser member is outside the body; and wherein the reservoir is secured to the body in the working positions and the withdrawn position;
    a displaceable elongated rigid member connecting the reservoir to the body, the rigid member comprising a first end that is slidably mounted in a guide rail formed over at least a portion of the height of the body, and a second end connected to the reservoir, such that the reservoir remains secured to the body, including when the reservoir is in the withdrawn position.

10. The dispenser device according to claim 9, wherein the elongated rigid member is configured to allow the body and the reservoir to be positioned side by side when the reservoir is in the withdrawn position, thereby allowing access to the inside of the body through the opening.

11. The dispenser device according to claim 9, wherein the elongated rigid member is displaceable in translation and in rotation relative to the body.

12. The dispenser device according to claim 9, wherein the second end of the elongated rigid member is attached to the reservoir by a fastener ring.

13. The dispenser device according to claim 1, wherein said rigid rod is at least partially received in said body when said reservoir is in the two working positions.

* * * * *